United States Patent
Marguet et al.

(12)

(10) Patent No.: US 6,451,795 B1
(45) Date of Patent: Sep. 17, 2002

(54) 4-OXO-3,5-DIHYDRO-4H-PYRIDAZINO[4,5-B] INDOLE-1-CARBOXAMIDE DERIVATIVES, PREPARATION AND THERAPEUTIC USE

(75) Inventors: Frank Marguet, Verrieres le Buission; Jacques Froissant, Moree; Régine Bartsch-Li, Fontenay aux Roses; Benoît Marabout, Chilly Mazarin; Mireille Sevrin, Paris, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/889,984

(22) PCT Filed: Jan. 21, 2000

(86) PCT No.: PCT/FR00/00134

§ 371 (c)(1),
(2), (4) Date: Jul. 25, 2001

(87) PCT Pub. No.: WO00/44751

PCT Pub. Date: Aug. 3, 2000

(30) Foreign Application Priority Data

Jan. 26, 1999 (FR) ............................................. 99 00805

(51) Int. Cl.[7] ................ A61K 31/5025; A61K 31/5377; C07D 487/04
(52) U.S. Cl. ..................... 514/248; 514/232.8; 544/115; 544/234
(58) Field of Search ................................. 544/234, 115; 514/248, 232.8

(56) References Cited

FOREIGN PATENT DOCUMENTS

| WO | 98/15552 | 4/1998 |
| WO | 99/06406 | 2/1999 |

OTHER PUBLICATIONS

Derwent Abstract 1998–240772 for WO 98/15552.
Derwant Abstract 1999–153682 for WO 99/06406.

*Primary Examiner*—Emily Bernhardt
(74) *Attorney, Agent, or Firm*—Paul E. Dupont; Michael D. Alexander

(57) ABSTRACT

4-Oxo-3,5-dihydro-4H-pyridazino[4,5-b]indole-1-carboxamide derivatives having affinity for the peripheral benzodiazepine receptors are useful for the prevention or treatment of peripheral neuropathies and for the treatment of central neurogenerative diseases.

9 Claims, No Drawings

4-OXO-3,5-DIHYDRO-4H-PYRIDAZINO[4,5-B] INDOLE-1-CARBOXAMIDE DERIVATIVES, PREPARATION AND THERAPEUTIC USE

A subject-matter of the present invention is compounds of general formula (I)

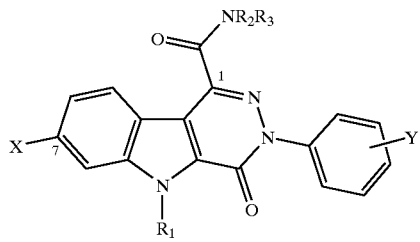

in which

X represents a hydrogen or halogen atom,

Y represents one or more atoms or groups chosen from hydrogen, halogens and methyl, methoxy and nitro groups, $R_1$ represents a ($C_1$–$C_4$) alkyl group, $R_2$ and $R_3$ each represent, independently of one another, a hydrogen atom or a ($C_1$–$C_4$) alkyl group or else $R_2$ and $R_3$ form, with the nitrogen atom which carries them, a pyrrolidinyl, piperidinyl or morpholinyl group.

The preferred compounds are those in the general formula of which X represents a halogen atom, Y represents a hydrogen atom or a halogen atom, $R_1$ represents a methyl group, $R_2$ represents a hydrogen atom or a methyl group and $R_3$ represents a methyl group or else $R_2$ and $R_3$ form, with the nitrogen atom which carries them, a pyrrolidinyl ring.

The compounds of general formula (I) can be prepared by processes illustrated by the following scheme:

Scheme

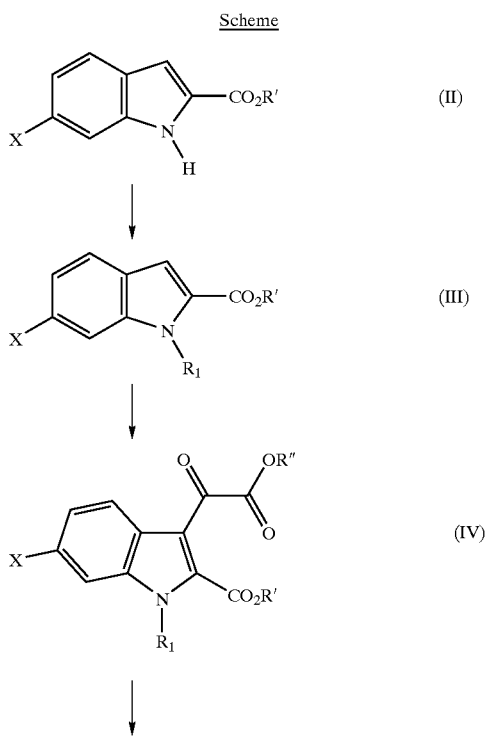

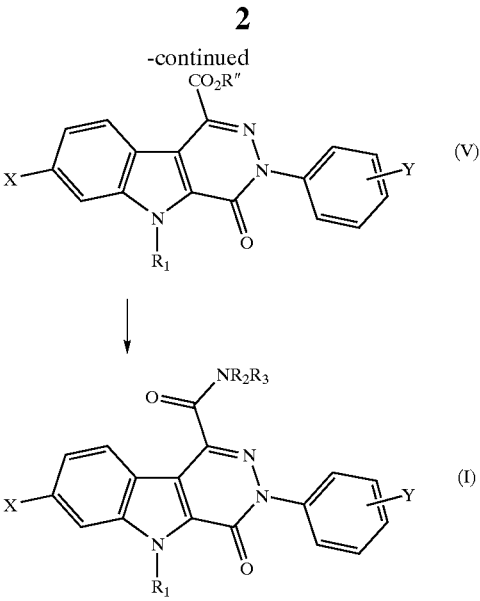

According to this scheme, a compound of general formula (II), in which X is as defined above and R' represents a $C_1$–$C_4$) alkyl group, is subjected to an alkylation reaction with a halide of general formula $HalR_1$, in which $R_1$ is as defined above, to result in a compound of general formula (III). This compound is subsequently reacted with a chlorooxoacetate of general formula $ClCOCO_2R''$, in which R" represents a ($C_1$–$C_4$) alkyl group, in a polar aprotic solvent, such as dichloroethane, at room temperature, in the presence of a Lewis acid, for example titanium tetrachloride, in order to obtain the diester of general formula (IV). The latter is subsequently treated in acetic acid, first at room temperature and then at the reflux temperature, with a phenylhydrazine optionally substituted by a Y group as defined above, in order to obtain an ester of general formula (V). Finally, this ester is converted to the secondary or tertiary amide of general formula (I) by the action of an amine of general formula $HNR_2R_3$, in which $R_2$ and $R_3$ are as defined above, for example in the presence of a trialkylaluminium derivative in a solvent such as toluene.

The starting compounds of general formula (II) are known to a person skilled in the art. By way of indication, mention will be made of the formation of 6-chloroindole-2-carboxylic acid derivatives according to Rydon et al., *J. Chem. Soc* (1955), 3499.

The examples which will follow illustrate the preparation of some compounds according to the invention. The elemental microanalyses and the I.R. and N.M.R. spectra confirm the structures of the compounds obtained.

The numbers shown between brackets in the titles of the examples correspond to those in the 1st column of the table given later.

In the names of the compounds, the dash "-" forms part of the word and the dash "-" is only used for the break at the line end; it is to be omitted in the absence of a break and must not be replaced either by a normal dash or by a space.

EXAMPLE 1

(Compound No. 8)

1-[[7-Chloro-3-(3-chlorophenyl)-5-methyl-4-oxo-3, 5-dihydro-4H-pyridazino[4,5-b]indol-1-yl]carbonyl] pyrrolidine

1.1. Ethyl 6-chloro-1-methyl-1H-indole-2-carboxylate

A suspension of 1.8 g (45 mmol) of 60% sodium hydride (washed beforehand with petroleum ether) and of 8.0 g (35.8 mmol) of ethyl 6-chloro-1H-indole-2-carboxylate in 80 ml of N,N-dimethylformamide is stirred for 2 h at room temperature, 2.8 ml (45 mmol) of iodomethane are subsequently added and the mixture is stirred at room temperature for 4 h. 5 ml of absolute ethanol are added and the solvent is evaporated under reduced pressure. The residue is taken up in water and the mixture is extracted with dichloromethane, the organic phase is dried and filtered, the solvent is evaporated under reduced pressure and the residue is purified by chromatography on a column of silica gel. 8.5 g (35.7 mmol) of a white crystalline compound are isolated.

Melting point: 75.5–76.5° C.

1.2. Ethyl 6-chloro-2-(ethoxycarbonyl)-1-methyl-α-oxo-1H-indole-3-acetate

A solution of 7.1 ml (63.6 mmol) of ethyl chlorooxoacetate in 100 ml of 1,2-dichloroethane is cooled to 0° C. 7.0 ml (63.6 mmol) of titanium tetrachloride are added in small portions and the mixture is stirred for 30 min at 0° C. A solution of 7.4 g (35.3 mmol) of ethyl 6-chloro-1-methyl-1H-indole-2-carboxylate is added and the mixture is stirred for 3 h at room temperature. The mixture is poured onto water and the organic phase is separated by settling, washed with dilute sodium hydroxide solution, dried over sodium sulphate and concentrated under reduced pressure to produce an oil which is purified by chromatography on a silica column (eluant: cyclohexane/dichloromethane: 2/8). 9.51 g (29.4 mmol) of compound are isolated in the form of a white solid.

Melting point: 94–95° C.

1.3. Ethyl 7-chloro-3-(3-chlorophenyl)-5-methyl-4-oxo-3,5-dihydro-4H-pyridazino[4,5-b]indole-1-carboxylate 7.0 g (39.1 mmol) of 3-chlorophenylhydrazine hydrochloride are dissolved in 50 ml of water and 5 ml of a 35% sodium hydroxide solution. Extraction is carried out with diethyl ether. The organic phase is dried over sodium sulphate, filtered and concentrated under reduced pressure. An oil is obtained, to which are added 100 ml of acetic acid and 4.0 g (12.35 mmol) of ethyl 6-chloro-2-(ethoxycarbonyl)-1-methyl-α-oxo-1H-indole-3-acetate. The reaction mixture is stirred for 30 min at room temperature and then for 6 h at reflux. The mixture is cooled, 100 ml of water are added and an insoluble material is collected by filtration, washed with water and purified by chromatography on a silica column (eluant: dichloromethane/ethyl acetate: 98/2). 4.59 g (11 mmol) of compound are isolated in the form of a white solid.

Melting point: 235.5–237.50° C.

1.4. 1-[[7-Chloro-3-(3-chlorophenyl)-5-methyl-4-oxo-3,5-dihydro-4H-pyridazino[4,5-b]indol-1-yl]carbonyl]pyrrolidine 5 ml (10 mmol) of a solution of trimethylaluminium (2M in toluene) in 80 ml of toluene are introduced under argon. The solution is cooled to 0° C. and then 0.84 ml (10 mmol) of pyrrolidine is added in small portions. After stirring for 20 min at room temperature, 0.5 g (1.2 mmol) of ethyl 7-chloro-3-(3-chlorophenyl)-5-methyl-4-oxo-3,5-dihydro-4H-pyridazino[4,5-b]indole-1-carboxylate is added and the mixture is heated at reflux for 3 h.

The solution is cooled to approximately 0° C. and the metal complex is slowly hydrolysed with water. 100 ml of dichloromethane are added and the solution is filtered. The precipitate is rinsed with dichloromethane, and 100 ml of water and 10 ml of a 1 M aqueous hydrochloric acid solution are added to the filtrate. The organic phase is separated by settling, washed with water, dried over sodium sulphate and concentrated under reduced pressure and the residue is purified by chromatography on a silica column (eluant: dichloromethane/ethyl acetate: 90/10).

After recrystallizing from a mixture of dichloromethane and ethyl acetate, 0.26 g (0.59 mmol) of compound is isolated in the form of a white solid with a fluffy appearance.

Melting point: 187–187.50° C.

EXAMPLE 2

(Compound No. 6)

7-Chloro-3-(3-chlorophenyl)-N,N,5-trimethyl-4-oxo-3,5-dihydro-4H-pyridazino[4,5-b]indole-1-carboxamide 0.815 g (10 mmol) of dimethylamine hydrochloride is introduced into 100 ml of toluene under argon, the solution is cooled to 0° C. and then 5 ml (10 mmol) of a trimethylaluminium solution (2M in toluene) are added in small portions. After stirring for 2 h at room temperature, 0.8 g (1.92 mmol) of ethyl 7-chloro-3-(3-chlorophenyl)-5-methyl-4-oxo-3,5-dihydro-4H-pyridazino[4,5-b]indole-1-carboxylate is added and the mixture is heated at reflux for 5 h. The solution is cooled to approximately 0° C. and the metal complex is slowly hydrolysed with water. 100 ml of dichloromethane are added and the solution is filtered. The precipitate is rinsed with dichloromethane, and 100 ml of water and 10 ml of a 1 M aqueous hydrochloric acid solution are added to the filtrate. The organic phase is separated by settling, washed with water, dried over sodium sulphate and concentrated under reduced pressure. The residue is purified by chromatography on a silica column (eluant: dichloromethane/ethyl acetate: 80/20). After recrystallizing from ethyl acetate, 0.43 g (1.0 mmol) of compound is isolated in the form of a white solid.

Melting point: 212.5–213.5° C.

EXAMPLE 3

(Compound No. 10)

7-Chloro-N,N,5-trimethyl-4-oxo-3-phenyl-3,5-dihydro-4H-pyridazino[4,5-b]indole-1-carboxamide

3.1. Ethyl 7-chloro-5-methyl-4-oxo-3-phenyl-3,5-dihydro-4H-pyridazino [4,5-b]indole-1-carboxylate The preparation is carried out as in Example 1.3. from 2.0 g (18 mmol) of phenylhydrazine and from 4.6 g (14.21 mmol) of ethyl 6-chloro-2-(ethoxycarbonyl)-1-methyl-α-oxo-1H-indole-3-acetate in 100 ml of acetic acid.

After reacting, the mixture is cooled, 100 ml of water are added and an insoluble material is isolated by filtration and is washed with water. It is purified by chromatography on silica (eluant: dichloromethane/ethyl acetate: 99/1). 2.98 g (7.8 mmol) of compound are isolated in the form of a white solid.

Melting point: 216–218.5° C.

3.2. 7-Chloro-N,N,5-trimethyl-4-oxo-3-phenyl-3,5-dihydro-4H-pyridazino[4,5-b]indole-1-carboxamide The preparation is carried out as in Example 2 from 0.815 g (10 mmol) of dimethylamine hydrochloride, from 5 ml (10 mmol) of a trimethylaluminium solution (2M in toluene) and from 0.74 g (1.94 mmol) of ethyl 7-chloro-5-methyl-4-oxo-3-phenyl-3,5-dihydro-4H-pyridazino[4,5-b]indole-1-carboxylate in 80 ml of toluene.

After reacting, the solution is cooled to approximately 0° C. and the metal complex is slowly hydrolysed with water. 100 ml of dichloromethane are added and the solution is filtered. The precipitate is rinsed with dichloromethane, and 100 ml of water and 10 ml of a 1M aqueous hydrochloric acid solution are added to the filtrate. The organic phase is separated by settling, washed with water, dried over sodium sulphate and concentrated under reduced pressure. The residue is purified by chromatography on a silica column (eluant: dichloromethane/ethyl acetate: 80/20).

After recrystallizing from a mixture of ethyl acetate and dichloromethane, 0.385 g (1.0 mmol) of compound is isolated in the form of a white solid.

Melting point: 254–255° C.

EXAMPLE 4

(Compound No. 5)

7-Chloro-N,N-diethyl-3-(3-methoxyphenyl)-5-methyl-4-oxo-3,5-dihydro-4H-pyridazino[4,5-b]indole-1-carboxamide

4.1. Ethyl 7-chloro-3-(3-methoxyphenyl)-5-methyl-4-oxo-3,5-dihydro-4H-pyridazino[4,5-b]indole-1-carboxylate The preparation is carried out as in Example 1.3. from 5.0 g (14.8 mmol) of 3-methoxyphenylhydrazine hydrochloride and from 4.7 g (14.5 mmol) of ethyl 6-chloro-2-(ethoxycarbonyl)-1-methyl-α-oxo-1H-indole-3-acetate in 25 ml of acetic acid.

After reacting, the mixture is cooled, 50 ml of water are added and an insoluble material is isolated by filtration and washed with water. It is purified by chromatography on a silica column (eluant: dichloromethane/ethyl acetate: 99/1). 4.89 g (11.9 mmol) of compound are isolated in the form of a white solid with a fluffy appearance.

Melting point: 182.5–183° C.

4.2. 7-Chloro-N,N-diethyl-3-(3-methoxyphenyl)-5-methyl-4-oxo-3,5-dihydro-4H-pyridazino[4,5-b]indole-1-carboxamide The preparation is carried out as in Example 1.4. from 1.04 g (10 mmol) of diethylamine, from 5 ml (10 mmol) of a trimethylaluminium solution (2M in toluene) and from 1.0 g (2.42 mmol) of ethyl 7-chloro-3-(3-methoxyphenyl)-5-methyl-4-oxo-3,5-dihydro-4H-pyridazino[4,5-b]indole-1-carboxylate in 100 ml of toluene.

The solution is cooled to approximately 0° C. and the metal complex is slowly hydrolysed with water. 100 ml of dichloromethane are added and the solution is filtered. The precipitate is rinsed with dichloromethane, and 100 ml of water and 10 ml of a 1M aqueous hydrochloric acid solution are added to the filtrate. The organic phase is separated by settling, washed with water, dried over sodium sulphate and concentrated under reduced pressure. The residue is purified by chromatography on a silica column (eluant: dichloromethane/ethyl acetate: 95/5). After recrystallizing from diethyl ether, 0.83 g (1.89 mmol) of compound is isolated in the form of a white solid.

Melting point: 207.5–208.5° C.

EXAMPLE 5

(Compound No. 17)

7-Chloro-3-(3-fluorophenyl)-N,N,5-trimethyl-4-oxo-3,5-dihydro-4H-pyridazino[4,5-b]indole-1-carboxamide

5.1. Ethyl 7-chloro-3-(3-fluorophenyl)-5-methyl-4-oxo-3,5-dihydro-4H-pyridazino[4,5-b]indole-1-carboxylate The preparation is carried out as in Example 1.3. from 2.0 g (12.3 mmol) of 3-fluorophenylhydrazine hydrochloride and from 1.75 g (5.4 mmol) of ethyl 6-chloro-2-(ethoxycarbonyl)-1-methyl-α-oxo-1H-indole-3-acetate in 100 ml of acetic acid.

After reacting, the mixture is cooled, 50 ml of water are added and an insoluble material is isolated by filtration and washed with water. It is purified by chromatography on a silica column (eluant: dichloromethane/ethyl acetate: 99/1). After recrystallizing from ethyl acetate, 1.65 g (4.13 mmol) of compound are isolated in the form of a white solid.

Melting point: 241–242° C.

5.2. 7-Chloro-3-(3-fluorophenyl)-N,N,5-trimethyl-4-oxo-3,5-dihydro-4H-pyridazino[4,5-b]indole-1-carboxamide.

The preparation is carried out as in Example 2 from 0.65 g (8 mmol) of dimethylamine hydrochloride, from 4 ml (8 mmol) of a trimethylaluminium solution (2M in toluene) and from 0.65 g (1.63 mmol) of ethyl 7-chloro-3-(3-fluorophenyl)-5-methyl-4-oxo-3,5-dihydro-4H-pyridazino[4,5-b]indole-1-carboxylate in 60 ml of toluene.

After reacting, the solution is cooled to approximately 0° C. and the metal complex is slowly hydrolysed with water. 100 ml of dichloromethane are added and the solution is filtered. The precipitate is rinsed with dichloromethane, and 100 ml of water and 10 ml of a 1 M aqueous hydrochloric acid solution are added to the filtrate. The organic phase is separated by settling, washed with water, dried over sodium sulphate and concentrated under reduced pressure. The residue is purified by chromatography on a silica column (eluant: dichloromethane/ethyl acetate: 90/10). After recrystallizing from ethyl acetate, 0.415 g (1.04 mmol) of compound is isolated in the form of a white solid.

Melting point: 208–209° C.

The chemical structures and the physical properties of some compounds according to the invention are illustrated in the following table. In the "Y", "$R_1$" and "$NR_2R_3$" columns, "Me" denotes a methyl group, "Et" denotes an ethyl group, "Piperid" denotes a piperidinyl group, "Pyrrolid" denotes a pyrrolidinyl group and "Morph" denotes a morpholinyl group.

TABLE (I)

| No. | X | Y | $R_1$ | $NR_2R_3$ | M.P. (° C.) |
|---|---|---|---|---|---|
| 1 | Cl | H | Me | $NEt_2$ | 197–199 |
| 2 | Cl | 3-Cl | Me | $NEt_2$ | 183.5–184.5 |
| 3 | Cl | 3-$NO_2$ | Me | $NEt_2$ | 223.5–224.5 |
| 4 | Cl | 3-Me | Me | $NEt_2$ | 190–190.5 |
| 5 | Cl | 3-Ome | Me | $NEt_2$ | 207.5–208.5 |
| 6 | Cl | 3-Cl | Me | $NMe_2$ | 212.5–213.5 |
| 7 | Cl | 3-Cl | Me | Piperid | 226–227 |
| 8 | Cl | 3-Cl | Me | Pyrrolid | 187–187.5 |
| 9 | Cl | 3-Ome | Me | $NMe_2$ | 250.5–251.5 |
| 10 | Cl | H | Me | $NMe_2$ | 254–255 |
| 11 | Cl | H | Me | Pyrrolid | 209–210 |
| 12 | Cl | H | Me | Piperid | 211–212 |
| 13 | Cl | 3-$NO_2$ | Me | $NMe_2$ | 260–261.5 |
| 14 | Cl | 2-Cl | Me | $NMe_2$ | 244–245 |
| 15 | Cl | 4-Cl | Me | $NMe_2$ | 282–283 |
| 16 | Cl | 3-Me | Me | $NMe_2$ | 233.5–234.5 |
| 17 | Cl | 3-F | Me | $NMe_2$ | 208–209 |
| 18 | Cl | 3,5-$(Cl)_2$ | Me | Pyrrolid | 222–224 |
| 19 | Cl | 3,5-$(Cl)_2$ | Me | Morph | 243–244 |

The compounds of the invention have been subjected to pharmacological tests which have demonstrated their advantage as substances possessing therapeutic activities.

Study of the [$^3$H]Ro5-4864 Binding to Peripheral Benzodiazepine (p) Sites

The affinity of the compounds of the invention for p sites (sites of peripheral-type binding for benzodiazepines) was determined.

The p-site receptors can be selectively labelled in rat kidney membranes incubated in the presence of [$^3$H]Ro5-4864. The compounds formed the subject of an in vitro study with regard to their affinity for these receptors.

The animals used are male Sprague-Dawley rats (Iffa Credo) weighing from 180 to 300 g. After decapitation, the kidney is removed and the tissue is homogenized at 4° C. using a Polytron® homogenizer for 2 min at 6/10 of the maximum speed in 35 volumes of $Na_2HPO_4$ 50 mM phosphate buffer at a pH adjusted to 7.5 with $NaH_2PO_4$. The membrane homogenate is filtered through gauze and diluted 10 times with buffer. [$^3$H]Ro5-4864 (Specific activity: 70–90 Ci/mmol; New England Nuclear), at a concentration of 0.5 nM, is incubated in the presence of 100 1 of the membrane homogenate in a final volume of 1 ml of buffer comprising the test compound.

After incubating for 3 h at 0° C., the membranes are recovered by filtering through Whatman GF/B® filters, which are washed with 2 times 4.5 ml of cold (0° C.) incubation buffer. The amount of radioactivity retained by the filter is measured by liquid scintigraphy. The percentage of inhibition of the binding of the [$^3$H]Ro5-4864 and then the $IC_{50}$ concentration, the concentration which inhibits 50% of the specific binding, are determined for each concentration of compound studied. The $IC_{50}$ values of the most active compounds range from 0.2 nM to 5 nM.

Study of the Neurotrophic Activity

The neurotrophic activity is evaluated in the rat in the test of regeneration of the injured facial nerve by measuring the functional recovery of the palpebral reflex according to a modification of the method of K. Kujawa et al., *Experimental Neurology* (1989), 105, 80–85.

Injury to the facial nerve by local freezing results in a degeneration of the distal part of the facial nerve and a loss in the blinking function of the eyelid.

The products to be studied are administered intraperitoneally or orally twice daily with an interval of 6 to 8 h every day for 10 days (duration of the experiment). The first treatment is administered 30 min before the injury.

Observation of the Animals

The recovery of the function of the eyelids in the injured animals is observed every day, once in the morning from D0 to D5 and twice (morning and evening with an interval of 6 to 8 h) from D6 to D10, before each treatment, according to a theoretical score ranging from 0 to 4.

Score 0: open eye, score 1: eye closed with a degree of less than half the eye; score 2: degree of closure of between 2 and :; score 3: degree of closure of greater than :; score 4: eye completely closed. The results are expressed by the ratio of the AUC (area under the curve) values of the treated group and of the control group.

The AUC ratios of the most active compounds lie between 1.10, and 1.20. These compounds therefore increase by 10 to 20% the recovery of the palpebral reflex after injury to the facial nerve.

The results of the tests show that the compounds of general formula (I) promote nerve regeneration. They can therefore be used in the preparation of medicaments intended for the prevention and treatment of peripheral neuropathies of various types, such as traumatic or ischaemic neuropathies, infectious, alcoholic, medicinal or genetic neuropathies, and motor neuron diseases, such as spinal amyotrophies and amyotrophic lateral sclerosis. These medicaments will also find an application in the treatment of neurodegenerative diseases of the central nervous system, either of acute type, such as strokes and cranial and medullar traumas, or of chronic type, such as autoimmune diseases (multiple sclerosis), Alzheimer's disease, Parkinson's disease and any other disease in which the administration of neurotrophic factors is supposed to have a therapeutic effect.

To this end, they can be presented in any pharmaceutical dosage form, alone or in combination with other neurotrophic, neuroprotective or immunomodulating compounds and with excipients appropriate for enteral or parenteral administration, for example in the form of tablets, dragées, capsules, including hard gelatin capsules, solutions or suspensions to be taken orally or injected, such as syrups or vials, transdermal patches, suppositories, and the like, comprising doses to allow a daily administration of 1 to 1000 mg of active substance.

What is claimed is:

1. A compound of formula (I)

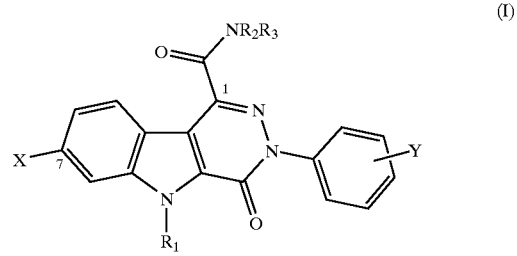

(I)

wherein:
X is hydrogen or halogen,
Y is hydrogen or one or more substituents selected from halogen, methyl, methoxy and nitro, R₁ is (C₁–C₄) alkyl, R₂ and R₃ are independently hydrogen or (C₁–C₄) alkyl, or R₂ and R₃ together with the nitrogen atom to which they are attached represent a pyrrolidinyl, piperidinyl or morpholinyl group.

2. A compound according to claim 1, wherein X is halogen, Y is hydrogen or one or more halogens, R₁ is methyl, R₂ is hydrogen, or methyl and R₃ is methyl or R₂ and R₃ together with the nitrogen atom to which they are attached represent a pyrrolidinyl group.

3. A compound selected from the group consisting of

1-[[7-Chloro-3-(3-chlorophenyl)-5-methyl-4-oxo-3,5-dihydro-4H-pyridazino[4,5-b]indol-1-yl]carbonyl] pyrrolidine, 1-[(7-chloro-3-phenyl-5-methyl4-oxo-3,5-dihydro4H-pyridazino[4,5-b]indol-1-yl)carbonyl]pyrrolidine, and 1-[[7-chloro-3-(3,5-dichlorophenyl)-5-methyl-4-oxo-3,5-dihydro-4H-pyridazino[4,5-b]indol-1-yl]carbonyl] pyrrolidine.

4. A pharmaceutical composition comprising a compound according to claim 1 in combination with an excipient.

5. A pharmaceutical composition comprising a compound according to claim 2 in combination with an excipient.

6. A pharmaceutical composition comprising a compound according to claim 3 in combination with an excipient.

7. A method for the treatment of peripheral neuropathies which comprises administering to a patient in need thereof a therapeutically effective amount of a compound according to claim 1.

8. A method for the treatment of peripheral neuropathies which comprises administering to a patient in need thereof a therapeutically effective amount of a compound according to claim 2.

9. A method for the treatment of peripheral neuropathies which comprises administering to a patient in need thereof a therapeutically effective amount of a compound according to claim 3.

* * * * *